(12) United States Patent
Boulanger

(10) Patent No.: US 10,953,174 B2
(45) Date of Patent: Mar. 23, 2021

(54) PNEUMATIC NO DELIVERY DEVICE

(71) Applicant: Air Liquide Santé (International), Paris (FR)

(72) Inventor: Thierry Boulanger, Media, PA (US)

(73) Assignee: L'Air Liquide, Société Anonyme pour l'Etude et l'Exploitation des Procédés Georges Claude, Paris (FR)

(*) Notice: Subject to any disclaimer, the term of this patent is extended or adjusted under 35 U.S.C. 154(b) by 198 days.

(21) Appl. No.: 16/110,161

(22) Filed: Aug. 23, 2018

(65) Prior Publication Data

US 2019/0083724 A1    Mar. 21, 2019

Related U.S. Application Data

(60) Provisional application No. 62/560,541, filed on Sep. 19, 2017.

(51) Int. Cl.
- *A61M 16/00* (2006.01)
- *A61M 16/20* (2006.01)
- *A61M 16/12* (2006.01)

(52) U.S. Cl.
CPC .... *A61M 16/0078* (2013.01); *A61M 16/0084* (2014.02); *A61M 16/12* (2013.01); *A61M 16/207* (2014.02); *A61M 16/208* (2013.01); *A61M 2202/0208* (2013.01); *A61M 2202/0275* (2013.01)

(58) Field of Classification Search
CPC ...... A61M 2202/0275; A61M 16/0084; A61M 16/12; A61M 16/207; A61M 16/208; A61M 16/0078
See application file for complete search history.

(56) References Cited

U.S. PATENT DOCUMENTS

| | | | |
|---|---|---|---|
| 3,941,168 A * | 3/1976 | Hiller | B67D 7/0484 |
| | | | 141/46 |
| 4,082,093 A * | 4/1978 | Fry | A61M 16/00 |
| | | | 128/204.25 |
| 4,091,783 A * | 5/1978 | Laprade | F02D 41/0027 |
| | | | 123/700 |

(Continued)

FOREIGN PATENT DOCUMENTS

FR        2824479 A1 * 11/2002    ............ A61M 15/00

*Primary Examiner* — Joseph D. Boecker
*Assistant Examiner* — Thomas W Greig
(74) *Attorney, Agent, or Firm* — Allen E. White

(57) ABSTRACT

The present invention concerns a pneumatic delivery device having three successively-arranged chambers, a membrane element arranged in the third chamber so as to ensure a tight separation of the third chamber into a lower chamber and upper chamber, a membrane element arranged between the second chamber and the lower chamber of the third chamber so as to ensure a tight separation between said lower chamber and second chamber, a stem integrally fixed to the first membrane element and to the second membrane element, a valve cooperating with an outlet orifice arranged between the first chamber and the second chamber, and a flow adjustment element arranged on a gas conduct in fluid communication with the gas outlet of the second chamber, said flow adjustment element being operable by a user for setting a quantity of gas circulating in said gas conduct.

11 Claims, 9 Drawing Sheets

(56) References Cited

U.S. PATENT DOCUMENTS

| | | | | |
|---|---|---|---|---|
| 4,575,042 | A | * | 3/1986 | Grimland .............. A61M 16/20 |
| | | | | 128/204.26 |
| 5,360,000 | A | * | 11/1994 | Carter ................... A61M 16/20 |
| | | | | 128/204.26 |
| 5,558,083 | A | | 9/1996 | Bathe et al. |
| 6,237,594 | B1 | * | 5/2001 | Davenport ............ A61M 16/20 |
| | | | | 128/204.26 |
| 2012/0097879 | A1 | * | 4/2012 | Gilbert ................... B65D 83/14 |
| | | | | 251/309 |
| 2014/0251329 | A1 | * | 9/2014 | Bostick ............... A61M 16/122 |
| | | | | 128/203.12 |
| 2014/0261415 | A1 | * | 9/2014 | Acker ................. A61M 16/024 |
| | | | | 128/203.14 |
| 2015/0202400 | A1 | * | 7/2015 | Clemensen ............ A61B 5/097 |
| | | | | 600/431 |
| 2017/0095633 | A1 | * | 4/2017 | Falligant ................ A61M 11/00 |

* cited by examiner

PNEUMATIC NO DELIVERY DEVICE

CROSS REFERENCE TO RELATED APPLICATIONS

This application claims the benefit of priority under 35 U.S.C. § 119 (a) and (b) to U.S. Provisional Patent Application No. 62/560,541 filed Sep. 19, 2017, the entire contents of which are incorporated herein by reference.

BACKGROUND

The invention concerns a pneumatic delivery device for gas delivery, in particular adapted and designed to be connected to a source of gaseous nitric oxide (NO) and the breathing pathway of a resuscitation bag.

Nitric Oxide (hereafter NO) is a colorless gas which, when inhaled, dilates the pulmonary blood vessels and increases oxygenation by improving gas exchanges in the lungs. These properties of NO are used for treating several medical conditions, such as Persistent Pulmonary Hypertension of the Newborn (PPHN) or Acute Respiratory Distress Syndrome (ARDS).

NO gas is usually mixed in low amounts to a respiratory oxygen-containing gas inhaled by a patient, according to a posology set by a physician. Usually, the $O_2$-containing gas is a $N_2/O_2$ mixture or air. Typically, the NO concentration in the gas, after mixing, is of between 5 and 100 ppm in volume (ppmv), depending on the treated population of patients, e.g. infants or adults.

The gas inhaled by the patient, that contains NO and oxygen, is usually delivered by the mean of a specific delivery device usually connected to a mechanical ventilator as described by U.S. Pat. No. 5,558,083. This delivery device, which is connected to gas cylinders containing a mixture of nitrogen ($N_2$) and NO containing between 200 and 800 ppmv of NO, generally includes an injection module located in the inspiratory line of a breathing circuit, whose distal ends are respectively connected to a mechanical ventilator and a patient.

The injection module includes a flow sensor which measures the flow delivered by the mechanical ventilator and sends back the measure to the NO delivery device, which computes and determines the right amount of NO to be delivered, based on the desired posology.

The delivery of NO is performed by the mean of a proportional solenoid valve in association to a dedicated flow sensor, e.g. internal to the delivery device, and supplied to the NO injection module via a dedicated gas line. The administration is continuous in a way that the delivery device continuously receives the measure of flow spreading into the inspiratory line of the breathing circuit and adjusts in real time the amount of NO to be delivered with respect to the set posology. In other word, whatever the flow delivered to the patient, this flow contains the right NO concentration.

However, there are many situations where NO therapies are initiated without the use of such devices. This is particularly true in emergency situations, either at the very place of the emergency or during transportation in mobile unit. In these situations, medical teams rely on a pneumatic delivery device, such as a NO blender, in conjunction with a resuscitation bag to perform mechanical ventilation.

Typically, the pneumatic delivery device is connected to two sources of gas, namely an oxygen supply and a cylinder containing NO as described above. In such a system, the user sets both a flow of oxygen, for instance between 5 to 15 L/min and a NO concentration of between 5 to 40 ppmv to add the right amount of NO coming from the NO cylinder. The resulting flow feeds the oxygen line of the resuscitation bag on which insufflations are performed to deliver mechanical ventilation to the patient.

Such a NO-administration mode suffers severe drawbacks which can impact the efficacy of the NO therapy.

The supply of NO is constant and independent on the minute ventilation of the patient, e.g. the depth (volume) and rate of insufflations with the resuscitation bag Indeed, the reserve of gas of the resuscitation bag is a mix of oxygen, at a given NO concentration, and air drawn from ambient. The balance of the mixture is determined by the depth and rate of the insufflations: it is therefore almost impossible to deliver the right NO concentration to the patient.

The NO carrier is only oxygen which favors hyperoxic situations. For instance, one could privilege the consistency of the NO concentration, e.g. 20 ppmv, and set to this purpose a high oxygen flow, up to 15 L/min, to make sure the resuscitation bag is always filled with pure oxygen at the right NO concentration.

However, this will generate fractions of inspired O2 of 100% with, as a consequence, a potential harmful hyperoxia. This is especially true in the pediatric population (e.g. PPHN) or complex adult conditions, such as ARDS.

The NO carrier is oxygen which accelerates the formation of nitrogen dioxide ($NO_2$), that is a harmful compound. This $NO_2$ formation is even greater in a resuscitation bag as the ventilation is intermittent and the NO volume stagnates in the bag, thereby favoring the oxidation of NO by $O_2$ species.

In other words, while keeping in mind a simple pneumatic delivery device to work in conjunction with a resuscitation bag, it would be safer and relevant to deliver the right amount of NO independently of the depth and rate of mechanical insufflations and not rely on the oxygen source as the sole NO carrier.

SUMMARY

A goal of the present invention is to provide an improved pneumatic delivery device and a resuscitation bag system including it.

A solution according to the present invention concerns a pneumatic delivery device comprising:
- a first, a second and a third successively-arranged chambers,
- a first membrane element arranged in the third chamber so as to ensure a tight separation of said third chamber into a lower chamber and upper chamber,
- a second membrane element arranged between the second chamber and the lower chamber of the third chamber so as to ensure a tight separation between said lower chamber and second chamber,
- a stem integrally fixed to the first membrane element and to the second membrane element, and carrying a valve element cooperating with an outlet orifice arranged between the first chamber and the second chamber for controlling the passage of gas from the first chamber to the second chamber through said outlet orifice,
- a gas inlet in fluid communication with the first chamber for allowing gas to penetrate into the first chamber,
- a gas outlet in fluid communication with the second chamber for allowing gas to exit the second chamber,
- a first pressure inlet in fluid communication with the upper chamber of the third chamber, a second pressure inlet in fluid communication with the lower chamber of the third chamber, and a flow adjustment element arranged on a gas conduct in fluid communication with the gas outlet of the second chamber, said flow adjustment element being operable by a user for setting a quantity of gas circulating in said gas conduct.

The device according to the present invention can further comprise one or more of the following additional features:

the valve element comprises a needle valve.

the valve element comprises a needle valve having a first conical shape.

the outlet orifice arranged between the first and second chambers has a second conical shape fitting the first conical shape of the needle valve of the valve element.

the flow adjustment element comprises a variable orifice.

the flow adjustment element is actuated by a dial.

a first diameter of the first membrane element is greater than a second diameter of the second membrane element.

a low pressure regulator is arranged upstream of the first chamber.

the first membrane element and the second membrane element each comprise a deformable portion arranged around a non-deformable lower part forming a central portion of each membrane element, said non-deformable lower part embedding a rigid reinforcement element.

The invention further concerns a resuscitation bag system comprising:

a flexible insufflation bag comprising an inlet conduit in fluid communication with the flexible insufflation bag, a NO injection module arranged in the inlet conduit and a pneumatic delivery device according to the present invention fluidly connected to the NO injection module.

The resuscitation bag system according to the present invention can further comprise one or more of the following additional features:

the NO injection module comprises a gas injector comprising a plurality of gas nozzles.

the gas injector is arranged in the lumen of a cylinder or a tubular element.

Further, the present invention also concerns a method for treating a respiratory disease of the lungs in a patient, comprising providing a NO-containing gas to a patient in need thereof by means of a pneumatic delivery device according to the present invention, preferably by means of a resuscitation bag system including a pneumatic delivery device according to the present invention.

Preferably, said NO-containing gas dilates the pulmonary blood vessels of the lungs and/or increases the oxygenation and gas exchanges in the lungs of said patient.

Preferably, the respiratory disease is chosen among Persistent Pulmonary Hypertension of the Newborn (PPHN) and Acute Respiratory Distress Syndrome (ARDS).

Preferably, the patient is an adult, a child or a baby.

BRIEF DESCRIPTION OF THE DRAWINGS

For a further understanding of the nature and objects for the present invention, reference should be made to the following detailed description, taken in conjunction with the accompanying drawings, in which like elements are given the same or analogous reference numbers and wherein.

DESCRIPTION OF PREFERRED EMBODIMENTS

Figure 1:
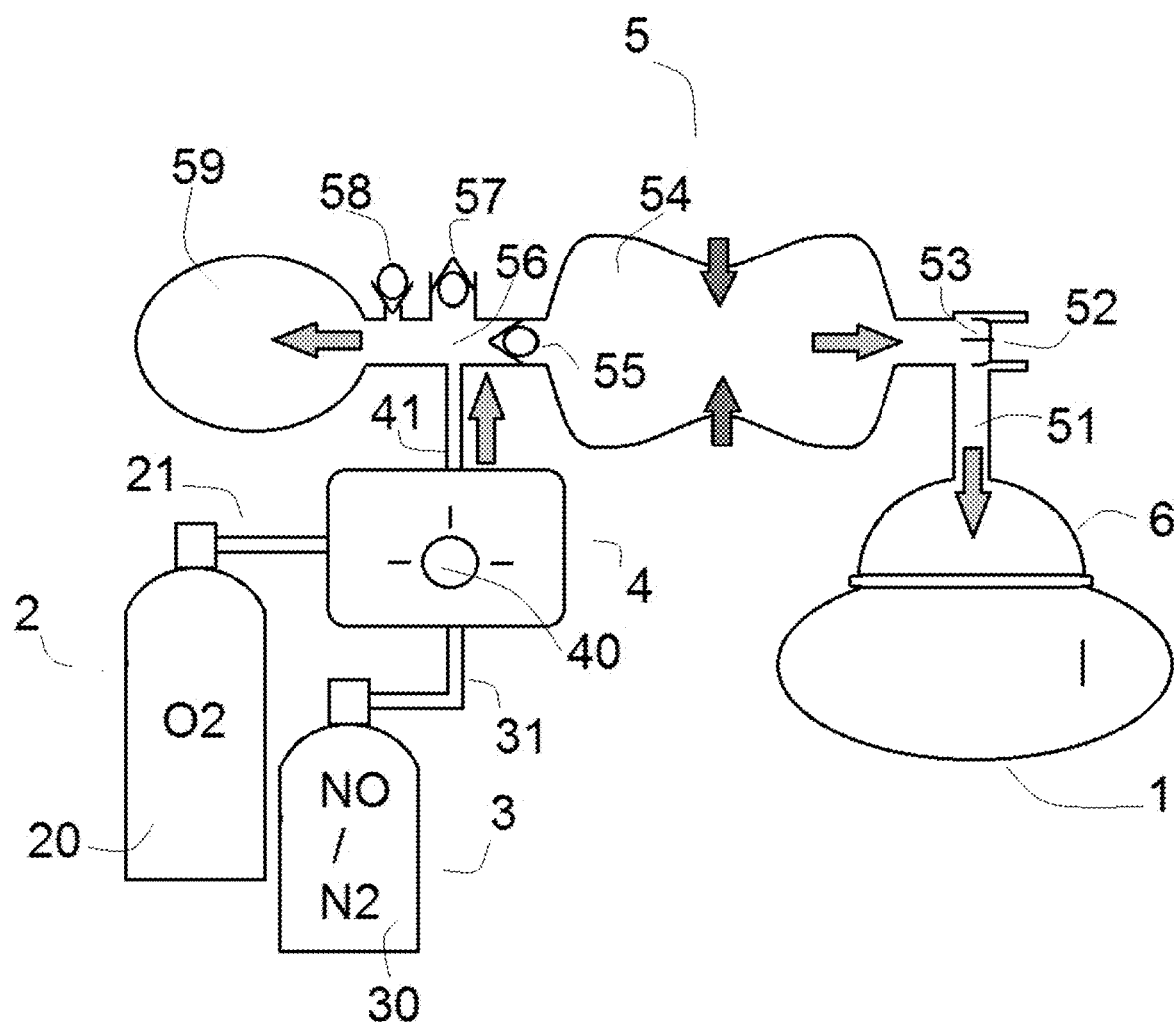
FIG. 1 shows a pneumatic device connected to a resuscitation bag system according to the prior art during the inspiration phase.

In FIG. 1, a patient 1 is connected to a resuscitation bag system 5 via a respiratory interface 6, such as a facial mask, a laryngeal mask or similar. The resuscitation bag system 5 comprises a flexible insufflation bag 54. A pneumatic device 4 is fluidly connected to the resuscitation bag system 5.

An oxygen source 2, typically a gas cylinder 20 containing medical grade oxygen, is fluidly connected via a first tubing 21 to the pneumatic device 4, whereas a NO source 3, typically a NO-gas cylinder 30 containing a mixture of medical grade $N_2$ and NO at a concentration of 800 ppmv (ppm in volume), is also fluidly connected via a second tubing 31 to the pneumatic device 4.

The pneumatic device 4 performs a $NO/O_2$ gas mixture based on the incoming oxygen flow provided by first tubing 21, typically a flow of between 5 and 15 L/min that is set by the operator, and a desired NO concentration that is also set by an operator, via a dial 40, which controls the amount of NO flowing into second tubing 31.

The pneumatic device 4 delivers a $NO/O_2$ flow into a third tubing 41. The $NO/O_2$ flow is the sum of the oxygen flow in the first tubing 21 and the NO flow in the second tubing 31 at a NO concentration set by dial 40, for instance 40 vol ppmv. Third tubing 41 is fluidly branched to inlet conduit 56 that is further connected to flexible insufflation bag 54.

In FIG. 1, the operator squeezes the flexible insufflation bag 54 to perform an insufflation of gas to the patient, which in turn leads valve 53 to occlude the exhalation port 52 and the volume displaced in insufflation bag 54 flows to the patient 1 via conduit 51 and interface 6. This phase generates a positive pressure which, as a result, forces one-way valve 55 to close and prevent the volume of insufflation bag 54 to flow backward to inlet conduit 56. In this case, the output flow in third tubing 41 enters into inlet conduit 56 and fills a reserve bag 59. Due to the slight positive pressure in inlet conduit 56, the one-way valve 57 is closed. In case the reserve 59 becomes over-distended a pressure build up will occur and the excess of pressure will be vented to ambient via safety valve 58.

Figure 2:
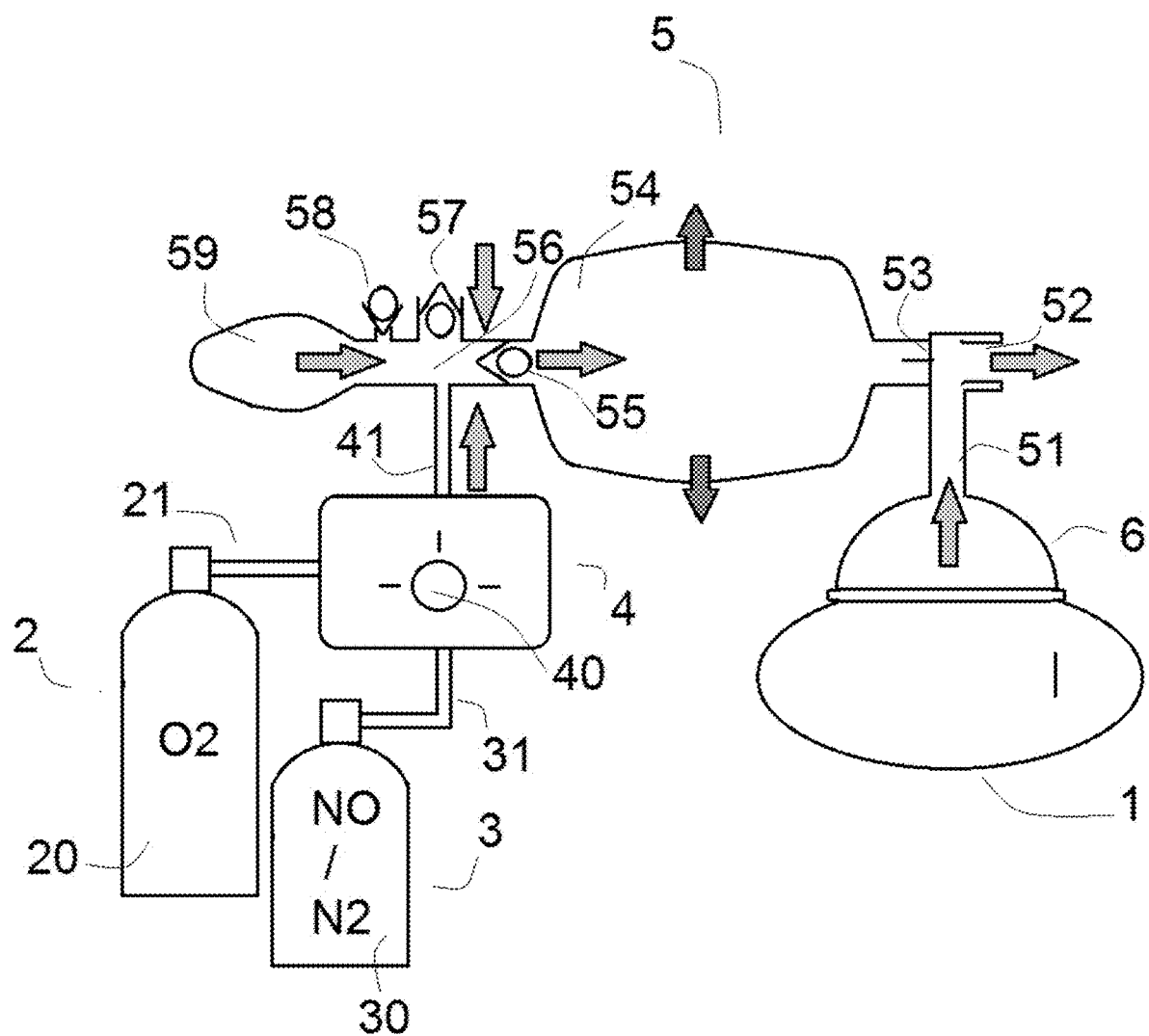
FIG. 2 shows a pneumatic device connected to a resuscitation bag system according to the prior art during the expiration phase.

FIG. 2 shows an expiration phase, when the operator has stopped squeezing insufflation bag 54 which enters in an expansion phase. This creates a negative pressure which holds back the valve 53 and liberates the exhalation port 52. The volume accumulated in patient 1, during the previous inspiratory phase, is then vented to the ambient atmosphere, via interface 6 and conduit 51.

At the same time, the negative pressure generated in insufflation bag 54 opens one-way valve 55, which will in turn direct flow from third tubing 41 into insufflation bag 54 via inlet conduit 56; empties reserve 59 into insufflation bag 54 via inlet conduit 56; and opens one-way valve 57 which allows ambient air flow to enter into insufflation bag 54, via inlet conduit 56.

With such a prior art system, it is not possible to accurately control the gas composition that is actually delivered to the patient 1.

For instance, if the oxygen set flow is 5 L/min, the accumulation in the reserve bag 59 and flow in third tubing 41 will not be sufficient to offset the negative pressure in insufflation bag 54 and consequently additional air from one-way valve 57 will enter in insufflation bag 54. Depending on the features of insufflation bag 54 (i.e., shape, material . . . ), the negative pressure will draw significant amounts of gas with dilution of up to 75% of NO concentration. As the volume entering insufflation bag 54 will next be administered to the patient 1 during the inspiratory phase, one can easily understand that the therapy will potentially be ineffective or at least less effective than desired.

Alternately, the operator can set a high flow of oxygen, for instance 15 L/min. If this setting does not prevent the one-way valve 57 to open and therefore to dilute the NO concentration, this flow, combined with the accumulated volume in reserve bag 59, will better offset the negative pressure in insufflation bag 54 and that the resulting NO concentration delivered to the patient will be roughly in the 25% range of the desired one. This is at the cost of high fraction of oxygen (almost 100 vol. %) which can have a harmful impact when administered to specific populations of patients, especially fragile patients, such as some babies or infants, including some toddlers.

Further, in those configurations, the formation of harmful $NO_2$ is unavoidable and accelerated by the contact of NO with high concentrations of oxygen. Indeed, NO and oxygen will coexist both in reserve bag 59 and insufflation bag 54 for durations that can greatly vary as the medical staff has to perform urgent care and only ventilates the patient every 30 seconds or the like. This situation is hazardous or detrimental for the patient as $NO_2$ is known to be detrimental even at ppmv levels, i.e. at less than 10 ppmv.

Figure 3A:
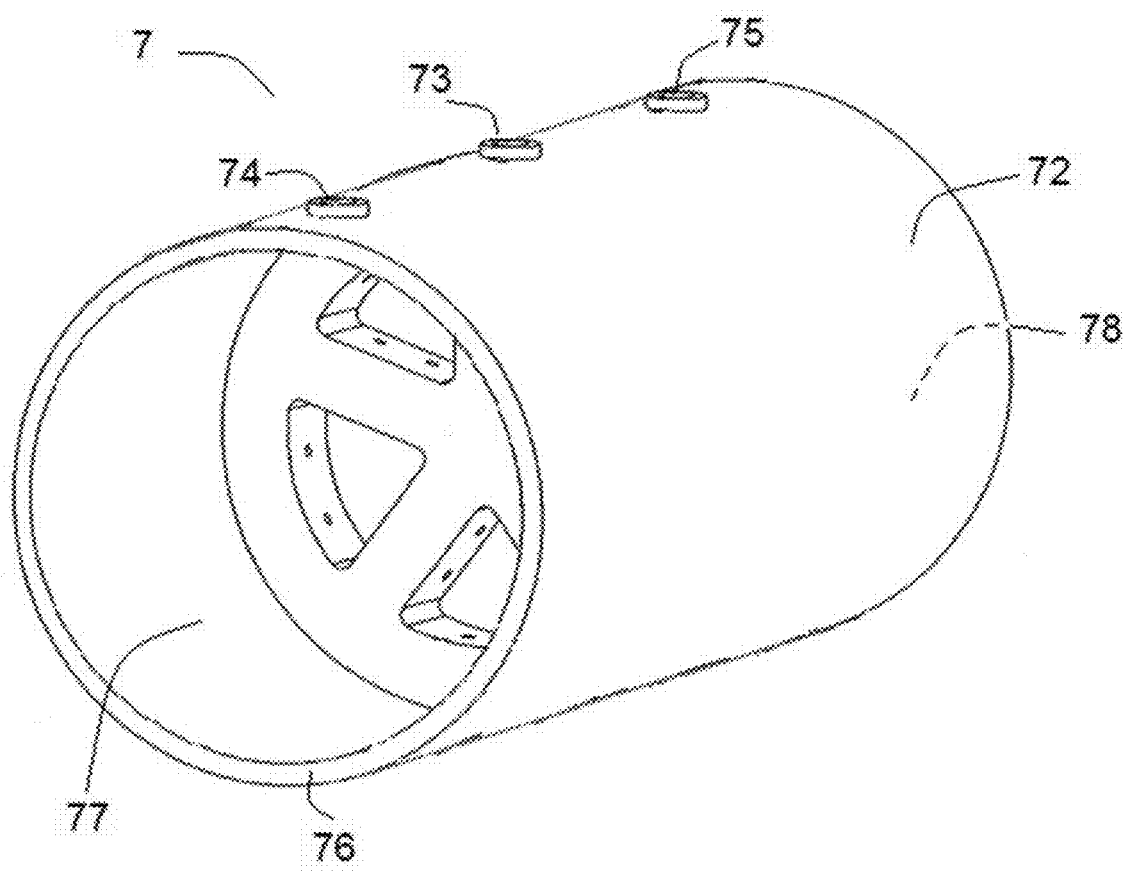
FIG. 3A shows an embodiment of a NO injector fluidly connected to a pneumatic delivery device according to the present invention.
Figure 3B:
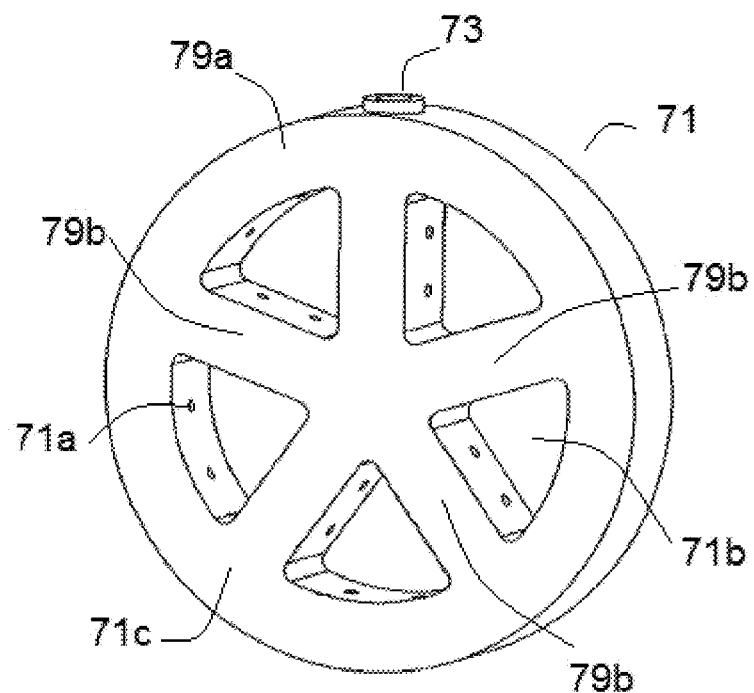
FIG. 3B shows an embodiment of a NO injector fluidly connected to a pneumatic delivery device according to the present invention.
Figure 3C:
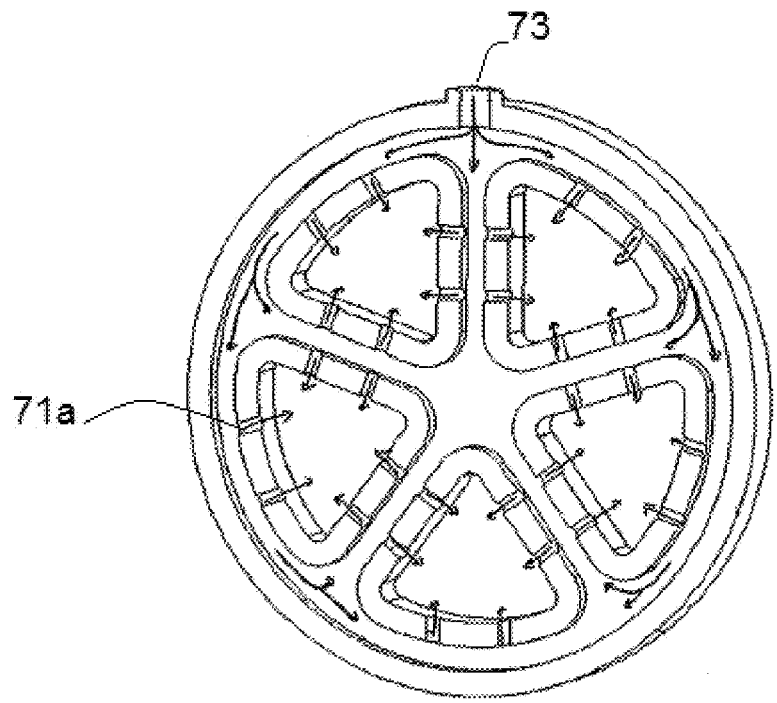
FIG. 3C shows an embodiment of a NO injector fluidly connected to a pneumatic delivery device according to the present invention.
Figure 7:
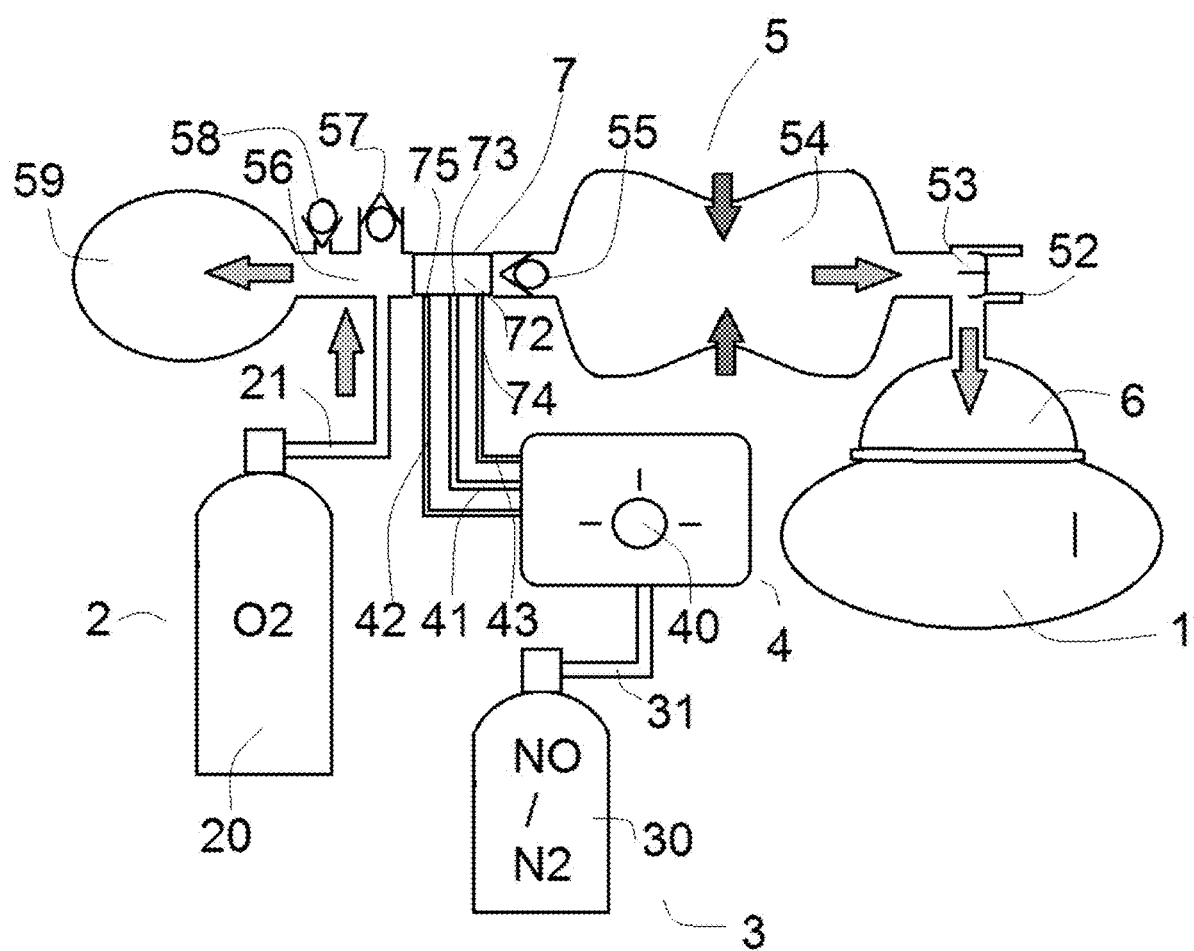
FIG. 7 illustrates the functioning of a pneumatic delivery device according to the present invention.
Figure 8:
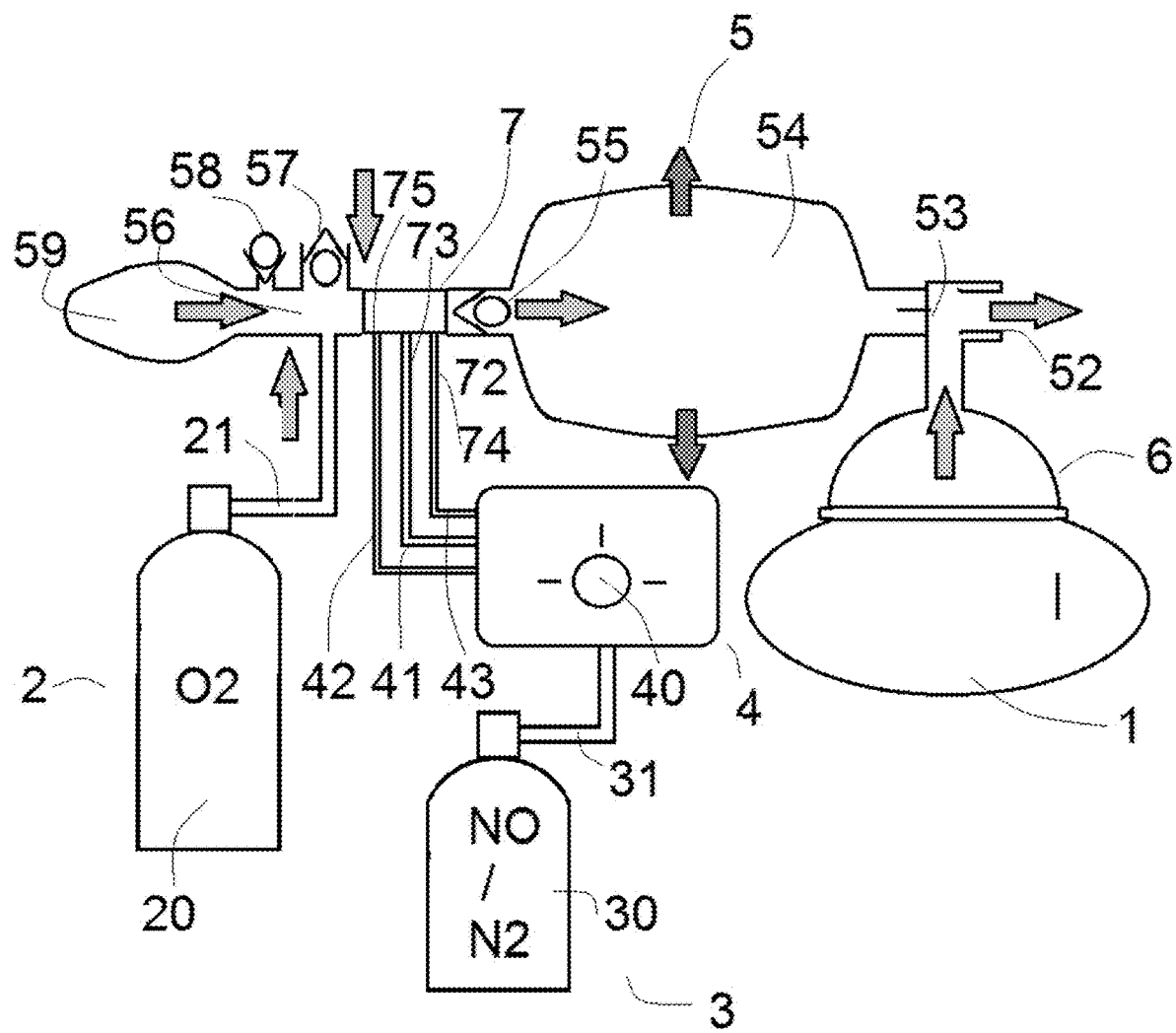
FIG. 8 illustrates the functioning of a pneumatic delivery device according to the present invention.

FIGS. 3A-3C shows an embodiment of a NO injection module 7 useable in connection with a pneumatic delivery device 4 according to the present invention, as described hereafter, in particular that can be inserted in the breathing circuit of a resuscitation bag system 5 according to the present invention (see FIGS. 7 and 8).

The principle of such a NO injection module 7 is disclosed in EP-A-2574394. It comprises a gas injector 71 arranged in the lumen 77 of a cylinder or a tubular element 72, traversed by a flow of respiratory gas. Gas injector 71 performs a fast homogeneous distribution of NO in the gaseous flow delivered to the patient in order to avoid local high concentrations of NO.

For doing it, the gas injector 71 comprises a hollow annular body 79a and hollow radial arms 79b in fluid communication with the hollow annular body 79a. Hollow annular body 79a and radial arms 79b carry a plurality of gas nozzles 71a that are designed for delivering gas in the lumen of the tubular element 72.

Actually, hollow annular body 79a and hollow radial arms 79b are fed with gas by a main port 73 as shown in FIG. 3C (cross sectional view) that traverses the peripheral wall 76 of tubular element 72 (FIG. 3A).

Hollow radial arms 79b are arranged in the center of hollow annular body 79a and spaced by windows 71b forming passages for the flow of gas circulating into the lumen of the tubular element 72.

The surface ratio between the plain surface 71c of hollow annular body 79a and radial arms 79b and windows 71b, as shown in FIG. 3B, determines the "resistance" of the injector 71 to flow propagation. This ratio creates a pressure drop that can be measured through an upstream port 75 and a downstream port 74 located on tubular element 72, in sites located upstream and downstream of injector 71. Upstream 75 and downstream 74 ports are arranged through the peripheral wall 76 of tubular element 72 and fluidly communicate with the lumen 77 of the tubular element 72.

Figure 4A:
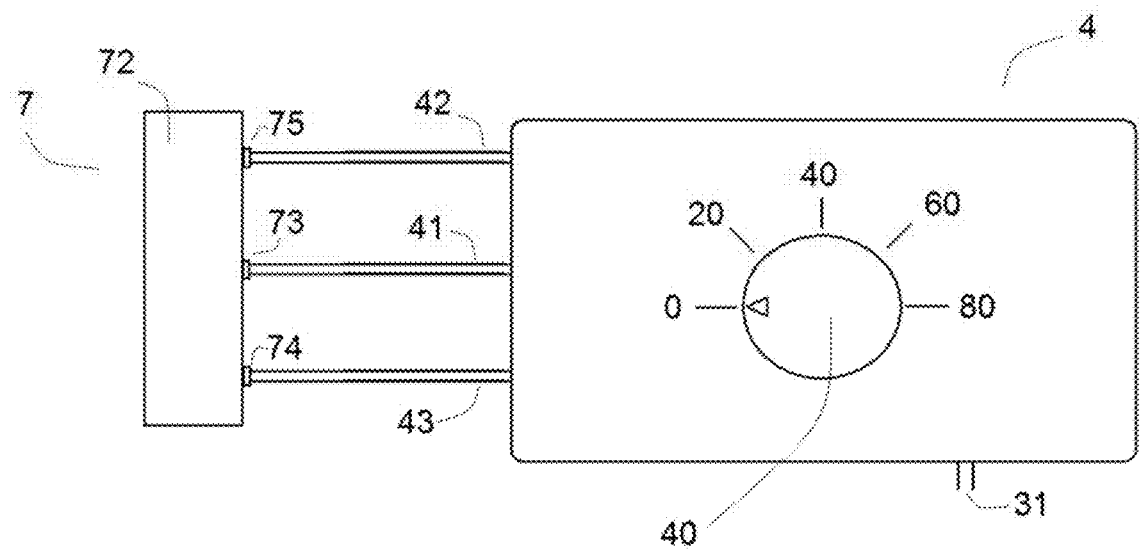
FIG. 4A represents an embodiment of a pneumatic delivery device according to the present invention.
Figure 4B:
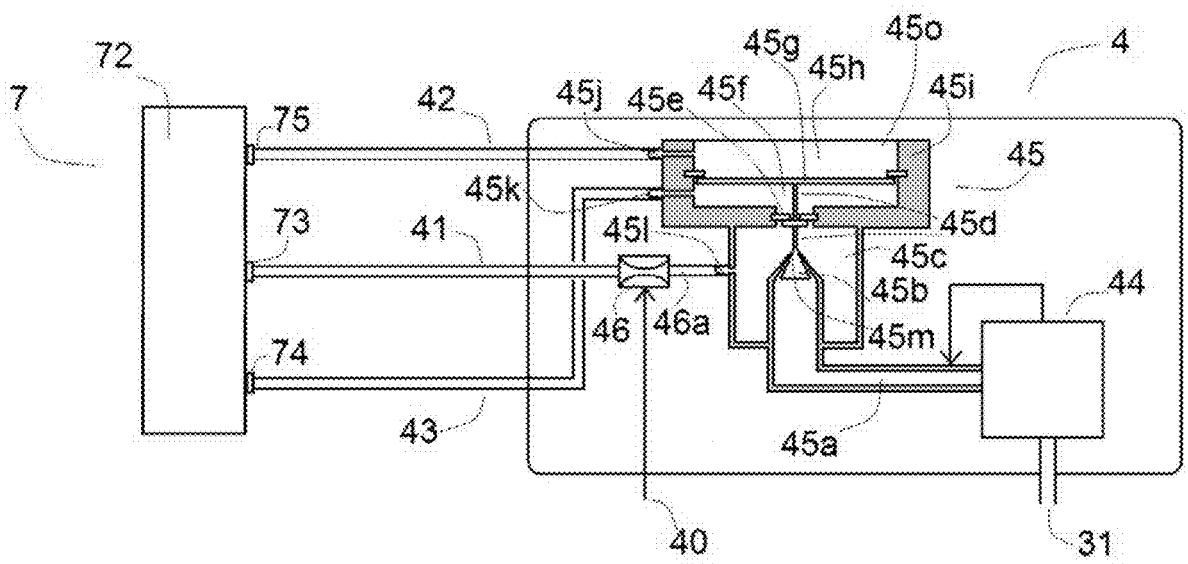
FIG. 4B represents an embodiment of a pneumatic delivery device according to the present invention.

FIGS. 4A-4B show an embodiment of a pneumatic system 4 according to invention that is fluidly connected to the upstream port 75 and downstream port 74 of the tubular element 72 of the NO injection module 7 of FIGS. 3A-3C, by means of pressure lines 42, 43, as well as to the main port 73 of tubular element 72 by means of gas line 41.

Pneumatic system 4 is fed with a $NO/N_2$ mixture by a first line 31 conveying a $NO/N_2$ mixture delivered by a gas cylinder 30 containing, for instance, 800 ppmv of NO diluted in nitrogen.

A dial 40 arranged on pneumatic system 4 can be actuated by the operator to select the desired NO concentration, for instance between 0 and 80 ppmv.

As detailed in FIG. 4B, first line 31, typically at 3.5 bar, is admitted into a low pressure regulator 44, such as the regulator "PRD2" commercialized by Beswick. At the pressure regulator 44 outlet, a constant pressure is obtained, typically of about 35 mbar, which will spread into the first chamber 45a of a main proportional module 45 that is arranged downstream of the low pressure regulator 44.

The main proportional module 45 further comprises a third chamber 45o divided into a lower chamber 45f and an upper chamber 45h arranged downstream of the first chamber 45a and the second chamber 45c.

When the flow into NO injection module 7 is equal to zero, the pressure values measured at upstream and downstream ports 75, 74 are equal, i.e. the same. These pressures will spread into the tubing 42, 43 and enter via connections 45j and 45k into the upper chamber 45h and lower chamber 45f of the main proportional module 45.

Figure 4C:
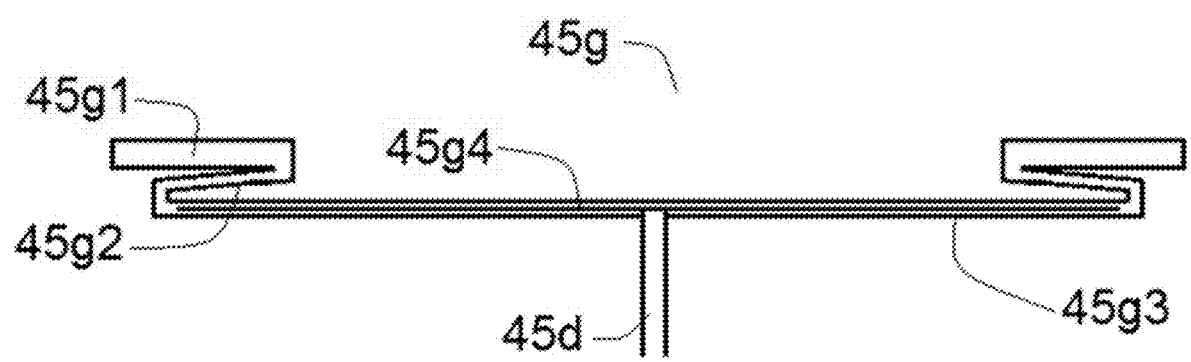
FIG. 4C represents an embodiment of the membrane elements of the pneumatic delivery device according to FIGS. 4A, 4B, and 5.

The lower 45f and upper 45h chambers of the main proportional module 45 are tightly separated by a first membrane element 45g that is detailed in FIG. 4C.

First membrane element 45g is made of a deformable material such as silicone, and has a first diameter of between about 2 and 6 cm. It comprises a lip portion 45g1 at its periphery, that is tightly and securely attached to the main structure 45i, i.e. one or several walls, delimiting the upper 45h and lower 45f chambers of the main proportional module 45.

A deformable portion 45g2 links the lip portion 45g1 to a lower part 45g3 or central portion of membrane. Said deformable portion 45g2 helps the lower part 45g3 of the membrane to move upwardly or downwardly depending on the pressure exerted on it, as explained hereafter.

The deformable portion 45g2 is arranged around the lower part 45g3 forming the central portion of the first membrane element 45g.

This lower part 45g3 of the membrane element 45g is not deformable as it embeds a rigid reinforcement element 45g4, such as a thin metallic or plastic sheet, or the like.

The rigid reinforcement element 45g4 carries a stem 45d, such as a little rod element of the like, that projects downwardly toward a second membrane element 45e, as shown in FIG. 4B.

Figure 4D:
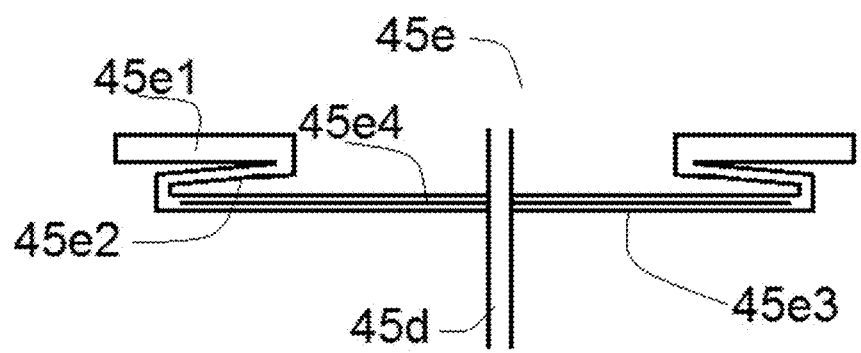
FIG. 4D represents an embodiment of the membrane elements of the pneumatic delivery device according to FIGS. 4A-4B and 5.

The second membrane element 45e has a structure that is roughly identical to the one of the first membrane element 45g, except that its second diameter is smaller, typically of about 1 cm, as shown in FIG. 4D.

It also comprises a lip portion 45e1 at its periphery, that is tightly and securely attached to the main structure 45i, a deformable portion 45e2 links the lip portion 45e1 to a lower part 45e3 or central portion of the second membrane 45e, and a rigid reinforcement element 45e4, such as a thin metallic or plastic sheet, or the like.

The second membrane element 45e is arranged between the second chamber 45c and the lower chamber 45f of the third chamber 45o, thereby ensuring a tight separation between said lower chamber 45f and second chamber 45c.

The second membrane element 45e is further traversed by stem 45d.

Actually, stem 45d is mechanically connected to a needle valve 45b as shown in FIG. 4B. Needle valve 45b has a conical shape. It can ensure a tight sealing between first and second chambers 45a and 45c as its conical shape fits with the conical surface of an outlet orifice 45m of first chamber 45a.

In case of equal pressures in chambers 45h and 45f, the first and second membrane elements 45g, 45e stay in their "at rest" position and the needle valve 45b occludes the outlet orifice 45m of the first chamber 45a. This is further amplified by the pressure existing in first chamber 45a, which generates an upward force further preventing any gas escape through outlet orifice 45m.

In contrast, when a gas flow is crossing the NO module 7, the gas injector 71 generates a pressure drop proportional to the gas flow. The difference of pressure between upstream port 75 and downstream port 74 becomes positive. By fluidic transmission, via tubings 42, 43 and connections 45j, 45k, a pressure differential occurs between upper and lower chambers 45h, 45f of the main proportional module 45. The pressure in upper chamber 45h becomes greater than the one in lower chamber 45f and this pressure differential creates an imbalance across the first membrane element 45g, which slightly moves downwardly as well as stem 45d by mechanical transmission of the movement.

The second membrane element 45e which is mechanically connected to stem 45d follows the downward movement.

As a consequence, the stem 45d lowers the needle valve 45b which, still partially occluding the conical portion of chamber 45a allows a little flow of NO crossing the outlet orifice 45m of the first chamber 45a. The exiting flow fills the second chamber 45c and exit through a connection 45l and a tubing 46a that is fluidly connected to gas line 41 that is fluidly connected to main port 73 of tubular element 72 thereby delivering a NO-containing gas to injector 71.

A variable orifice 46 controlled by the dial 40 is arranged in gas line 41 or in tubing 46a, such as a plate with multiple orifices or a manual needle valve controlled by a thread. Actuating the dial 40, for instance from "0" to "80" ppmv, changes the size of the variable orifice 46, i.e. the width for the passage of NO containing-gas, and thus the final NO concentration obtained afterwards.

The maximum size, i.e. diameter, of the orifice is set so as to limit the flow of gas exiting the second chamber 45c to 3 L/min, for instance, so as to ensure a safe delivery of gas. Considering a pressure of 35 mbar, a suitable maximum diameter can be of about 1 mm, which means that the orifice can progressively vary from 0 to 1 mm depending on the actuation of the dial 40.

Figure 5:
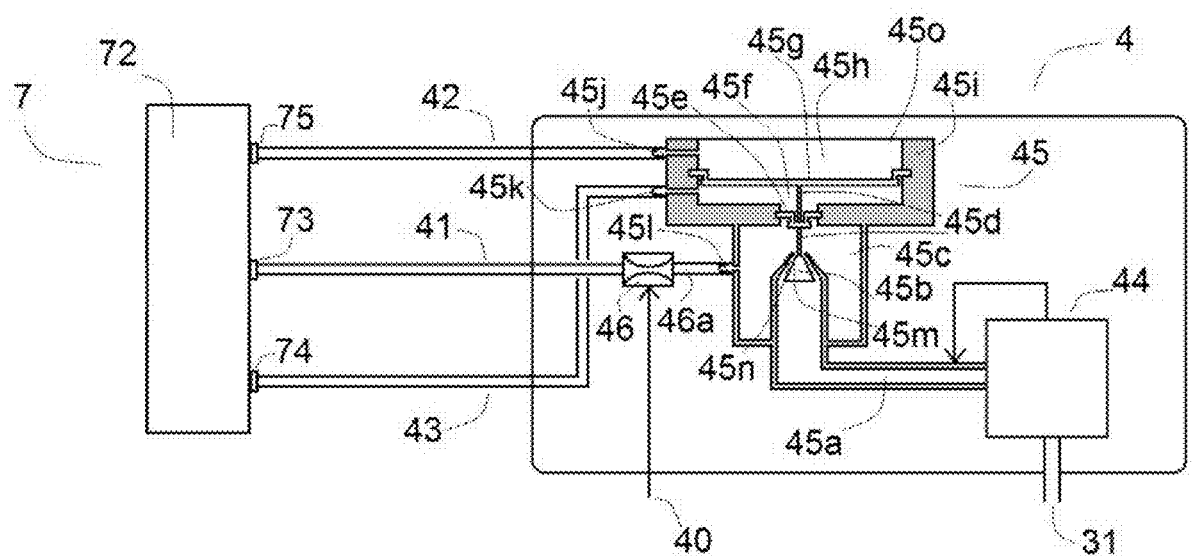
FIG. 5 represents an embodiment of a pneumatic delivery device according to the present invention.

FIG. 5 illustrates the case where a gas flow of 10 L/min (typically an $O_2/N_2$ mixture) crosses the NO module 7, whereas the dial 40 is positioned on "40 ppmv" of NO.

The gas flow creates a differential pressure of for example 2 mbar across the injector 71 and said differential of pressure is transmitted to upper and lower chambers 45h, 45f by gas lines 42, 43 as above explained, and causes a deformation of the first membrane element 45g, thereby creating a downward movement of stem 45d, of second membrane element 45e and of needle valve 45b as explained above, and allowing gas coming from the first chamber 45a to enter into the second chamber 45c, and fill it.

Figure 6:
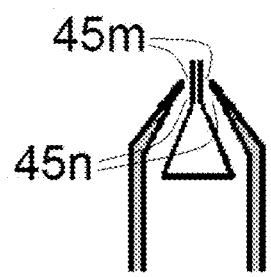
FIG. 6 shows an embodiment of the needle valve and the conical walls of the first chamber of the pneumatic delivery device according to FIGS. 4A, 4B, and 5.

The flowrate at which this occurs, depends on the resistance to flow of the variable orifice 46 and equivalent resistance of the exit orifice 45m and flow pathway 45n, as shown in FIG. 6, which is the thin passage between needle valve 45b and the conical walls of first chamber 45a.

The system is preferably designed so that the flow exiting the variable orifice 46 is of about 0.5 L/min. This flow is conveyed by tubing 41 to port 73, afterward mixed with the main gaseous flow circulating through the NO module 7, by means the plurality of nozzles 71a carried by the injector 71.

The gaseous mixture thus obtained contains about 40 ppmv of NO, the source of NO being a cylinder containing 800 ppmv of NO diluted in $N_2$.

Changing the concentration setting in actuating dial 40, but without modifying the position of needle valve 45b, modifies the gaseous flow exiting the second chamber 45c. For instance, setting a "80 ppmv" concentration further opens the orifice 46, e.g. decreases the pressure drop across orifice 46 and consequently increases the pressure differential between first and second chambers 45a, 45c, thereby increasing the flow passing through exit orifice 45m, i.e. doubling it up to 1 L/min, and further increasing the concentration in the main flow to 80 ppmv.

For a higher flow traversing the NO module 7, for example 30 L/min, the pressure differential in upper and lower chambers 45h and 45f is greater, for example of about 5 mbar, thereby further increasing the flow pathway volume 45n and thus the flow passing through outlet orifice 45m, as illustrated in FIG. 6.

FIG. 7 is similar to FIG. 1, except that the resuscitation bag 5 is now fluidly connected to a pneumatic system 4 according to the invention as shown in FIGS. 4A, 4B and 5.

More precisely, the oxygen source 2 (medical-grade $O_2$) is connected to inlet conduit 56 that is in fluid connection with the insufflation bag 54 of the resuscitation bag 5, whereas the NO source 3 (800 ppmv NO in medical-grade $N_2$) is connected to the pneumatic device 4 of the present invention. Inlet conduit 56 further comprises an additional air source, namely a one-way valve 57 allowing air to enter into inlet conduit 56, but preventing any gas escape.

A NO module 7 as shown in FIGS. 3A-3C is inserted in the resuscitation bag 5, between inlet conduit 56 and a one-way valve 55 located upstream of insufflation bag 54. Said NO module 7 is further fluidly connected to the pneumatic device 4 of the present invention as described in connection with FIGS. 4A, 4B and 5.

In FIG. 7, the operator squeezes the insufflation bag 54 to perform an insufflations of gas to the patient (i.e. inspiration phase) as described above, thereby generating a positive pressure which forces one-way valve 55 to close and prevent the volume of insufflation bag 54 to flow in the direction of the NO module 7 and inlet conduit 56. At the same time, O2 flow in tubing 21 enters into inlet conduit 56 and then fills the reserve bag 59.

Due to the slight positive pressure in inlet conduit 56, the one-way valve 57 is closed. In case where the reserve bag 59 becomes over distended a pressure build up will occur and the excess of pressure will be vented to ambient via a safety valve 58 located close to the inlet/outlet orifice of reserve bag 59. In other words, O2 is sent to either reservoir bag 59 or safety valve 58. One-way valve 55 being closed, no flow circulates into NO module 7, and no pressure differential exists between upstream port 75 and downstream port 74. As no pressure differential exists between, no NO is delivered by the pneumatic delivery device 4, as pressures in chambers 45h and 45f are equal, the first and second membrane elements 45g, 45e are in their "rest" position and the needle valve 45b occludes the outlet orifice 45m of the first chamber 45a.

FIG. 8 shows the expiration phase following the inspiration phase of FIG. 7. When the operator stops squeezing the insufflation bag 54, the latter enters in an expansion phase as it is a flexible bag. This creates a negative pressure which opens the one-way valve 55 and allows gas passing through inlet conduit 56 and NO module 7, in the direction of the insufflation bag 54, thereby emptying reserve bag 59 and refilling insufflation bag 54, and further allows one-way valve 57 to open and let ambient air flowing into insufflation bag 54 via inlet conduit 56 and NO module 7.

The gas mixture made of oxygen and additional air, when passing into the NO module 7, generates a positive pressure between upstream port 75 and downstream port 74. Said positive pressure involves, as above explained, a supply of NO by the pneumatic delivery device 4, which is mixed with the gas into the NO module 7 as the injector 71 of the NO module 7 homogeneously dilutes the NO gas in the main flow circulating into the NO module 7 in the direction of the insufflation bag 54.

The amount of NO thus delivered is proportional to the gas flow through the NO module 7 so that the NO concentration is kept constant during the expansion phase of insufflation bag 54. The NO-containing mixture stored in insufflation bag 54, at a desired NO concentration, is ready for the next insufflation phase.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as fall within the spirit and broad scope of the appended claims. The present invention may suitably comprise, consist or consist essentially of the elements disclosed and may be practiced in the absence of an element not disclosed. Furthermore, if there is language referring to order, such as first and second, it should be understood in an exemplary sense and not in a limiting sense. For example, it can be recognized by those skilled in the art that certain steps can be combined into a single step.

The singular forms "a", "an" and "the" include plural referents, unless the context clearly dictates otherwise.

"Comprising" in a claim is an open transitional term which means the subsequently identified claim elements are a nonexclusive listing (i.e., anything else may be additionally included and remain within the scope of "comprising"). "Comprising" as used herein may be replaced by the more limited transitional terms "consisting essentially of" and "consisting of" unless otherwise indicated herein.

"Providing" in a claim is defined to mean furnishing, supplying, making available, or preparing something. The step may be performed by any actor in the absence of express language in the claim to the contrary.

Optional or optionally means that the subsequently described event or circumstances may or may not occur. The description includes instances where the event or circumstance occurs and instances where it does not occur.

Ranges may be expressed herein as from about one particular value, and/or to about another particular value. When such a range is expressed, it is to be understood that another embodiment is from the one particular value and/or to the other particular value, along with all combinations within said range.

All references identified herein are each hereby incorporated by reference into this application in their entireties, as well as for the specific information for which each is cited.

What is claimed is:

1. A pneumatic delivery device (4) comprising:
   a first, a second and a third successively-arranged chambers (45a, 45c, 45o) wherein the chambers are successively-arranged as a first chamber, then a second chamber, and then a third chamber,
   a first membrane element (45g) arranged in the third chamber (45o) configured and adapted to ensure a tight separation of said third chamber (45o) into a lower chamber (45f) and upper chamber (45h),
   a second membrane element (45e) arranged between the second chamber (45c) and the lower chamber (45f) of the third chamber (45o) configured and adapted to ensure a tight separation between said lower chamber (45f) and second chamber (45c),
   a stem (45d) integrally fixed to the first membrane element (45g) and to the second membrane element (45e), and carrying a valve element (45b) cooperating with an outlet orifice (45m) arranged between the first chamber (45a) and the second chamber (45c) configured and adapted for controlling the passage of gas from the first chamber (45a) to the second chamber (45c) through said outlet orifice (45m),
   a gas inlet (31) in fluid communication with the first chamber (45a) configured and adapted for allowing gas to penetrate into the first chamber (45a),
   a gas outlet (45l) in fluid communication with the second chamber (45c) configured and adapted for allowing gas to exit the second chamber (45c),
   a first pressure inlet (45j) in fluid communication with the upper chamber (45h) of the third chamber (45o),
   a second pressure inlet (45k) in fluid communication with the lower chamber (45f) of the third chamber (45o), and
   a flow adjustment element (46) arranged on a gas conduct (46a) in fluid communication with the gas outlet (45l) of the second chamber (45c), said flow adjustment element (46) being operable by a user for setting a quantity of gas circulating in said gas conduct (46a).

2. The pneumatic delivery device of claim 1, wherein the valve element (45b) comprises a needle valve.

3. The pneumatic delivery device of claim 2, wherein the valve element (45b) comprises a needle valve having a first conical shape.

4. The pneumatic delivery device of claim 3, wherein the outlet orifice (45m) arranged between the first and second chambers (45a, 45c) has a second conical shape fitting a first conical shape of the needle valve of the valve element (45b).

5. The pneumatic delivery device of claim 1, wherein the flow adjustment element (46) comprises a variable orifice.

6. The pneumatic delivery device of claim 5, wherein the flow adjustment element (46) is actuated by a dial.

7. The pneumatic delivery device of claim 1, wherein a first diameter of the first membrane element (45g) is greater than a second diameter of the second membrane element (45e).

8. The pneumatic delivery device of claim 1, wherein a low pressure regulator (44) is arranged upstream of the first chamber (45a).

9. The pneumatic delivery device of claim 1, wherein the first membrane element (45g) and the second membrane element (45e) each comprise a deformable portion (45g2, 45e2) arranged around a non-deformable lower part (45g3, 45e3) forming a central portion of each membrane element (45g, 45e), said non-deformable lower part (45g3, 45e3) embedded with a rigid reinforcement element (45g4, 45e4).

10. A resuscitation bag system (5) comprising:
a flexible insufflation bag (54) comprising an inlet conduit (56) in fluid communication with the flexible insufflation bag (54),
a Nitric Oxide (NO) injection module (7) arranged in the inlet conduit (56) and
a pneumatic device (4) according to claim 1, fluidly connected to the NO injection module (72).

11. The resuscitation bag system (5) of claim 10, wherein the NO injection module (7) comprises a gas injector (71) comprising a plurality of gas nozzles (71a), said gas injector (71) being arranged in the lumen (77) of a cylinder or a tubular element (72).

* * * * *